US010961183B2

(12) United States Patent
Hu

(10) Patent No.: US 10,961,183 B2
(45) Date of Patent: *Mar. 30, 2021

(54) PROCESS FOR PRODUCING ALKALI TAURINATE

(71) Applicant: VITAWORKS IP, LLC, North Brunswick, NJ (US)

(72) Inventor: Songzhou Hu, Princeton, NJ (US)

(73) Assignee: VITAWORKS IP, LLC, North Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/030,605

(22) Filed: Jul. 9, 2018

(65) Prior Publication Data

US 2018/0312464 A1 Nov. 1, 2018

Related U.S. Application Data

(63) Continuation of application No. 15/870,844, filed on Jan. 12, 2018, now Pat. No. 10,040,755, which is a continuation of application No. PCT/US2017/018527, filed on Feb. 17, 2017, which is a continuation of application No. 15/228,539, filed on Aug. 4, 2016, now Pat. No. 9,573,890, which is a continuation-in-part of application No. 14/120,651, filed on Jun. 12, 2014, now Pat. No. 9,428,451, which is a continuation-in-part of application No. 14/120,046, filed on Apr. 18, 2014, now Pat. No. 9,428,450.

(51) Int. Cl.
C07C 303/02 (2006.01)
C07C 303/32 (2006.01)
C07C 303/44 (2006.01)
C07C 303/22 (2006.01)
C07C 309/14 (2006.01)
B01J 23/04 (2006.01)

(52) U.S. Cl.
CPC .......... *C07C 303/32* (2013.01); *C07C 303/02* (2013.01); *C07C 303/22* (2013.01); *C07C 303/44* (2013.01); *C07C 309/14* (2013.01); *B01J 23/04* (2013.01)

(58) Field of Classification Search
None
See application file for complete search history.

(56) References Cited

U.S. PATENT DOCUMENTS

| | | | | |
|---|---|---|---|---|
| 1,932,907 A * | 10/1933 | Nicodemus | ........... | C07C 309/14 562/102 |
| 1,999,614 A * | 4/1935 | Ossenbeck | ........... | C07C 309/14 562/104 |
| 2,109,401 A | 2/1938 | Nicodemus | | |
| 2,693,488 A | 11/1954 | Sexton | | |
| 2,820,818 A | 1/1958 | Sexton | | |
| 8,609,890 B1 | 12/2013 | Hu | | |
| 9,061,976 B1 | 6/2015 | Hu | | |
| 9,108,907 B1 | 8/2015 | Hu | | |
| 9,428,450 B2 | 8/2016 | Hu | | |
| 9,428,451 B2 | 8/2016 | Hu | | |
| 9,573,890 B2 | 2/2017 | Hu | | |
| 9,593,076 B2 | 3/2017 | Hu | | |
| 9,598,357 B1 | 3/2017 | Hu | | |
| 9,598,360 B2 | 3/2017 | Hu | | |
| 9,745,258 B1 | 8/2017 | Hu | | |
| 9,815,778 B1 | 11/2017 | Hu | | |
| 9,850,200 B1 | 12/2017 | Hu | | |
| 9,926,265 B1 | 3/2018 | Hu | | |
| 9,994,517 B1 | 6/2018 | Hu | | |
| 10,040,755 B2 | 8/2018 | Hu | | |
| 10,071,955 B1 | 9/2018 | Yong et al. | | |
| 10,112,894 B2 | 10/2018 | Hu | | |
| 10,131,621 B2 | 11/2018 | Hu | | |
| 2014/0121405 A1* | 5/2014 | Chen | ..................... | C07C 303/18 562/104 |
| 2015/0210633 A1 | 7/2015 | Hu | | |
| 2015/0299113 A1 | 10/2015 | Hu | | |
| 2016/0340300 A1 | 11/2016 | Hu | | |
| 2016/0355470 A1 | 12/2016 | Hu | | |
| 2018/0093946 A1 | 4/2018 | Hu | | |
| 2018/0141899 A1 | 5/2018 | Hu | | |
| 2018/0155278 A1 | 6/2018 | Hu | | |
| 2018/0162806 A1 | 6/2018 | Hu | | |
| 2019/0112260 A1 | 4/2019 | Hu | | |
| 2019/0112261 A1 | 4/2019 | Hu | | |

(Continued)

FOREIGN PATENT DOCUMENTS

CN  101486669 A  7/2009
CN  101508657 A  8/2009

(Continued)

OTHER PUBLICATIONS

Database Caplus Chemical Abstracts Service, Columbus, Ohio, US; Database Accession No. 1986:34336, Abstractor DD 219023 Bach et al., Feb. 20, 1985 (Year: 1985).*
Liu Fuming, China Chemical Trade, Process Design of Taurine, Year 2013, p. 120, vol. 5, No. 6, China National Chemical Center, Beijing City, China (Year: 2013).*
Journal of Hubei Institute of Technology, Opimization on Ammonolysis in Manufacturing Method of Taurine,Year 2004, pp. 23-26 , vol. 19, No. 1, Sum No. 66, Editorial Department of Journal of Hubei Polytechnic University, Wuhan, China (Year: 2004).*
English translation of WO 0177071 (Year: 2001).*
WO 01/77071, English Translation (Year: 2001).*
Wu Jiang et al., Optimization on Ammonolysis in Manufacturing Method of Taurine, 19:1, Journal of Hubei Polytechnic University 23-26 (2004) English Translation (Year: 2004).*

(Continued)

Primary Examiner — Karl J Puttlitz
(74) Attorney, Agent, or Firm — Myers Wolin, LLC

(57) ABSTRACT

There is disclosed a process for producing alkali taurinate by the ammonolysis of alkali ditaurinate, alkali tritaurinate, or a solution of alkali ditaurinate and alkali tritaurinate in the presence of one or more catalysts. The ammonolysis reaction is catalyzed by alkali salts of hydroxide, sulfate, sulfite, phosphate, or carbonate.

9 Claims, No Drawings

(56) References Cited

U.S. PATENT DOCUMENTS

| | | | |
|---|---|---|---|
| 2019/0112262 | A1 | 4/2019 | Hu |
| 2019/0135739 | A1 | 5/2019 | Hu |

FOREIGN PATENT DOCUMENTS

| | | | | |
|---|---|---|---|---|
| CN | 101508658 | A | | 8/2009 |
| CN | 101508659 | A | | 8/2009 |
| CN | 101717353A | A | | 6/2010 |
| CN | 104945289 | A | | 9/2015 |
| CN | 105693559 | A | | 6/2016 |
| CN | 105732440 | A | | 7/2016 |
| CN | 106008280 | A | | 10/2016 |
| CN | 107056659 | A | | 8/2017 |
| DE | 219023 | | * | 2/1985 |
| DE | 219023 | A3 | | 2/1985 |
| WO | 0177071 | | * | 10/2001 |
| WO | 0177071 | A1 | | 10/2001 |

OTHER PUBLICATIONS

Liu Fuming, Process Design of Taurine Ammonolysis, 5:8 China Chemical Trade 120 (2013), English Translation (Year: 2013).*
German Patent DD 219023, translation (Year: 1985).*
Liu Fuming Process Design of the Ammonolysis Reaction of Taurine, China Chemical Trade, 2013, No. 8, pp. 120. (Original article is published in China in Chinese, a English translation by the Applicant is included).
Liu Fuming, Xie Liming Study on the Ammonolysis Reaction for Taurine, Shandong Chemical Industry, 2015, 44 (5), pp. 27-28,30. (Original article is published in Chinese. An English translation by the Applicant is included).
International Search Report for corresponding International Application No. PCT/CN2015/000232, dated Jul. 1, 2015.
Extended European Search Report and the European Search Opinion completed Apr. 5, 2017 for corresponding European Application No. 17157022.9.
USPTO Non-Final Office Action for corresponding U.S. Appl. No. 15/228,568 dated Oct. 5, 2016.
USPTO Non-Final Office Action for corresponding U.S. Appl. No. 14/120,651 dated Mar. 15, 2016.
International Search Report and Written Opinion for corresponding International Application No. PCT/US2017/018527, dated Jun. 8, 2017.
Japanese Notice of Reasons for Rejection, dated Jun. 13, 2017 with English machine translation, for corresponding Japan application No. 2017-033759.
USPTO Non-Final Office Action for corresponding U.S. Appl. No. 15/228,539 dated Oct. 17, 2016.
USPTO Non-Final Office Action for corresponding U.S. Appl. No. 15/120,046 dated Aug. 26, 2015.
Canadian First Office Action, dated Nov. 2, 2017 for corresponding Canada Application No. 2,946,181.
Office Action issued by the Canadian Intellectual Property Office for corresponding Canadian Patent Application No. 2,946,181, dated Mar. 26, 2018.
Notification of Reasons for Rejection issued by the Japan Patent Office for corresponding Japanese Patent Application No. 2017-505693, dated Mar. 27, 2018, with an English translation.
Extended European Search Report issued by the European Patent Office for corresponding European Patent Application No. EP181547902, dated Jun. 25, 2018.
USPTO Non-Final Office Action for corresponding U.S. Appl. No. 15/870,844 dated May 10, 2018.
Uspto Notice of Allowance for corresponding U.S. Appl. No. 15/870,844 dated Jun. 15, 2018.
*Hubei Grans Life Science and Technology Co., Ltd v. Vitaworks IP, LLC*, Case No. IPR2018-01766, Petition for Inter Parte Review of U.S. Pat. No. 9,428,450 Under 37 C.F.R. § 42.100, Sep. 28, 2018, pp. 80, Alexandria, Virginia.
*Hubei Grans Life Science and Technology Co., Ltd v. Vitaworks IP, LLC*, Case No. IPR2018-01767, Petition for Inter Parte Review of U.S. Pat. No. 9,428,451 Under 37 C.F.R. § 42.100, Sep. 28, 2018, pp. 88, Alexandria, Virginia.
*Hubei Grans Life Science and Technology Co., Ltd v. Vitaworks IP, LLC*, Case No. IPR2018-01768 Petition for Inter Parte Review of U.S. Pat. No. 9,573,890 Under 37 C.F.R. § 42.100, Sep. 28, 2018, pp. 82, Alexandria, Virginia.
Declaration of Mark A. Lipton in Support of Petition for Inter Partes Review of U.S. Pat. No. 9,428,450 Under 37 C.F.R. § 42.100, Sep. 28, 2018, pp. 65.
Declaration of Mark A. Lipton in Support of Petition for Inter Partes Review of U.S. Pat. No. 9,428,451 Under 37 C.F.R. § 42.100, Sep. 28, 2018, pp. 69.
Declaration of Mark A. Lipton in Support of Petition for Inter Partes Review of U.S. Pat. No. 9,573,890 Under 37 C.F.R. § 42.100, Sep. 28, 2018, pp. 66.
Bondavera et al., Pharmaceutical Chemistry Journal, Synthesis of Taurine, Mar. 2008, pp. 142-144, vol. 42, No. 3, Springer Science+Business Media, Inc, Secaucus, New Jersey.
Liu Fuming, China Chemical Trade, Process Design of Taurine, Year 2013, p. 120, vol. 5, No. 6, China National Chemical Center, Beijing City, China http://chemmedia.com.cn/GotoBin/Select.DLL.
Journal of Hubei Institute of Technology, Opimization on Ammonolysis in Manufacturing Method of Taurine,Year 2004, pp. 23-26, vol. 19, No. 1, Sum No. 66, Editorial Department of Journal of Hubei Polytechnic University, Wuhan, China.
Patent Owner's Preliminary Response for Inter Partes Review of U.S. Pat. No. 9,428,450 IPR2018-01766, dated Jan. 11, 2019, 50 pages.
Patent Owner's Preliminary Response for Inter Partes Review of U.S. Pat. No. 9,428,451 IPR2018-01767, dated Jan. 14, 2019, 62 pages.
Patent Owner's Preliminary Response for Inter Partes Review of U.S. Pat. No. 9,573,890 IPR2018-01768, dated Jan. 16, 2019, 54 pages.
Robert E. Maleczka's Declaration in Support of Patent Owner's Preliminary Response for Inter Partes Review of U.S. Pat. No. 9,428,450 IPR2018-01766, dated Jan. 11, 2019, 60 pages.
Robert E. Maleczka's Declaration in Support of Patent Owner's Preliminary Response for Inter Partes Review of U.S. Pat. No. 9,428,451 IPR2018-01767, dated Jan. 14, 2019, 75 pages.
Robert E. Maleczka's Declaration in Support of Patent Owner's Preliminary Response for Inter Partes Review of U.S. Pat. No. 9,573,890 IPR2018-01768, dated Jan. 16, 2019, 67 pages.
Patent Owner's Response for Inter Partes Review of U.S. Pat. No. 9,428,450, IPR2018-01766, dated Jul. 12, 2019, 36 pages.
Robert E. Maleczka's 2nd Declaration in Support of Patent Owner's Response for Inter Partes Review of U.S. Pat. No. 9,428,450, IPR2018-01766, dated Jul. 12, 2019, 81 pages, Vitaworks Exhibit 2007.
Curriculum Vitae (CV) of Robert E. Maleczka, as of Jul. 12, 2019, 39 pages, Vitaworks Exhibit 2008.
Decision re Institution of Inter Partes Review issued for Case IPR2018-01766 for corresponding U.S. Pat. No. 9,428,450, Dated Apr. 9, 2019, 45 pages.
Decision re Institution of Inter Partes Review issued for Case IPR2018-01767 for corresponding U.S. Pat. No. 9,428,451, dated Apr. 10, 2019, 25 pages.
Decision re Institution of Inter Partes Review issued for Case IPR2018-01768 for corresponding U.S. Pat. No. 9,573,890, dated Apr. 10, 2019, 23 pages.
Objective Indicia filed with Response dated Jul. 25, 2019, 11 pages.
Results for experiments conducted between May 14, 2019 and Jun. 30, 2019, Vitaworks Exhibits 2009-2065.
Objective Indicia Exhibit A: Excerpt from "Bulletin of Ministry of Environment Protection of China", Jan. 27, 2015, with English summary, and excerpt from "Environment Impact Assessment Report of 25,000/Year Taurine Plant of Hubei Grand Life Science and Technology Co. Ltd.", dated Jul. 24, 2017, with English summary.
Objective Indicia Exhibit B: "Production Flowchart of Taurine in Environmental Impact Assessment Report of Jiangying Huachang Food Additive Company", 2005, with English translation of flowchart.

(56) References Cited

OTHER PUBLICATIONS

Objective Indicia Exhibit C: "Production Flowchart of Taurine in Amended Environmental Impact Assessment Report of Jiangying Huachang Food Additive Company", 2017, with English translation of flowchart.
Objective Indicia Exhibit D: Selected pp. from Qiangjiang Yongan Pharmaceutical Co. Annual Reports 2012-2015, with partial English translations.
Objective Indicia Exhibit G: "Study of the Ammonolysis Reaction for Taurine" Liu 2015; Liu Fuming & Xie Liming, Shandong Chemical Industry, May 2015, vol. 44, No. 5, pp. 27-28, 30, with English translations.
Objective Indicia Exhibit H: Liu 2013, Liu Fuming, China Chemical Trade Monthly Journal, Aug. 2013, vol. 5, Issue. 8, HGL Exhibit 1019.
Objective Indicia Exhibit I: Wu 2004, Wu Jiang & Guan Zailin J., Journal of Hubei Polytechnic University, Feb. 2004, vol. 19, No. 1, pp. 23-26, HGL Exhibit 1016.
Petitioner's Reply to Patent Owner's Response for Inter Partes Review of U.S. Pat. No. 9,428,450, IPR2018-01766, dated Oct. 7, 2019, 38 pages.
Patent Owner's Surreply for Inter Partes Review of U.S. Pat. No. 9,428,450, IPR2018-01766, dated Nov. 15, 2019, 33 pages.
Final Written Decision for Inter Partes Review of U.S. Pat. No. 9,428,450, IPR2018-01766, dated Apr. 2, 2020, 65 pages.
Declaration of Mark A. Lipton in Support of Peitioner's Reply to Patent Owner's Response dated Oct. 7, 2019, 33 pages.
Declaration of Joe P. Foley, Ph.D. In Support of Peitioner's Reply to Patent Owner'S Response, dated Oct. 7, 2019, 34 pages.
Notice of Allowance issued by the United States Patent and Trademark Office for corresponding U.S. Appl. No. 14/120,046, dated May 24, 2016.
Notice of Allowance issued by the United States Patent and Trademark Office for corresponding U.S. Appl. No. 14/120,046, dated Jul. 14, 2016.
Notice of Allowance issued by the United States Patent and Trademark Office for corresponding U.S. Appl. No. 15/238,621, dated Oct. 5, 2016.
Non-Final Office Action issued by the United States Patent and Trademark Office for corresponding U.S. Appl. No. 15/228,539, dated Oct. 17, 2016.
Final Office Action issued by the United States Patent and Trademark Office for corresponding U.S. Appl. No. 14/120,046, dated Dec. 8, 2015.
Notice of Allowance issued by the United States Patent and Trademark Office for corresponding U.S. Appl. No. 15/228,539, dated Dec. 23, 2016.
Notice of Allowance issued by the United States Patent and Trademark Office for corresponding U.S. Appl. No. 15/238,621, dated Jan. 4, 2017.
Notice of Allowance issued by the United States Patent and Trademark Office for corresponding U.S. Appl. No. 15/228,568, dated Jan. 17, 2017.
Notice of Allowance issued by the United States Patent and Trademark Office for corresponding U.S. Appl. No. 14/120,651, dated Aug. 2, 2016.
Maleczka, R. E., Supplemental Declaration of Robert E. Maleczka, Jr., Ph.D., IPR2018-01766, Exhibit 2006, 8 pages.
Protest Under 37 C.F.R. 1.291(a) against Reissue U.S. Appl. No. 16/843,272, Dated Jul. 17, 2020, 14 pages.
Protest Under 37 C.F.R. 1.291(a) against Reissue U.S. Appl. No. 16/854,395, Dated Jul. 17, 2020, 14 pages.
Protest Under 37 C.F.R. 1.291(a) against Reissue U.S. Appl. No. 16/854,406, Dated Jul. 17, 2020, 14 pages.
Protest Under 37 C.F.R. 1.291(a) against Reissue U.S. Appl. No. 16/842,389, Dated Jul. 28, 2020, 20 pages.
Protest Under 37 C.F.R. 1.291(a) against Reissue U.S. Appl. No. 16/863,384, Dated Aug. 3, 2020, 26 pages.
Notice of Allowance, Reissue U.S. Appl. No. 16/843,272, dated Aug. 25, 2020, 12 pages.
Notice of Allowance, Reissue U.S. Appl. No. 16/854,406, dated Aug. 26, 2020, 12 pages.
Non-Final Office Action of Reissue U.S. Appl. No. 16/863,384 for U.S. Pat. No. 9,428,451 B2, dated Sep. 22, 2020, 34 pages.
Non-Final Office Action of Reissue U.S. Appl. No. 16/842,389 for U.S. Pat. No. 9,573,890 B2, dated Sep. 22, 2020, 31 pages.
Non-Final Office Action of Reissue U.S. Appl. No. 16/853,395 for U.S. Pat. No. 9,428,450 B2, dated Sep. 9, 2020, 26 pages.
Notice of Allowance of Reissue U.S. Appl. No. 16/842,389 for U.S. Pat. No. 9,573,890 B2, dated Oct. 21, 2020, 9 pages.
Notice of Allowance of Reissue U.S. Appl. No. 16/863,384 for U.S. Pat. No. 9,428,451 B2, dated Oct. 29, 2020, 8 pages.
Notice of Allowance of Reissue U.S. Appl. No. 16/854,395 for U.S. Pat. No. 9,428,450 B2, dated Oct. 29, 2020, 8 pages.

* cited by examiner

PROCESS FOR PRODUCING ALKALI TAURINATE

CROSS REFERENCE TO RELATED APPLICATIONS

This application is a continuation application of U.S. application Ser. No. 15/870,844, filed on Jan. 12, 2018, which is a continuation application of PCT/US2017/018527, filed on Feb. 17, 2017, which is a continuation application of U.S. application Ser. No. 15/228,539, filed on Aug. 4, 2016, now U.S. Pat. No. 9,573,890, which is a continuation-in-part of U.S. application Ser. No. 14/120,651, filed on Jun. 12, 2014, now U.S. Pat. No. 9,428,451, which is a continuation-in-part of U.S. application Ser. No. 14/120,046, filed on Apr. 18, 2014, now U.S. Pat. No. 9,428,450, the contents of each of which are incorporated herein by reference.

TECHNICAL FIELD

The present invention relates to a process for the production of taurine from alkali isethionate in a high overall yield (i.e., greater than 90% to nearly quantitative) by carrying out the ammonolysis reaction of alkali isethionate to alkali taurinate in the presence of alkali ditaurinate or alkali tritaurinate, or their mixture.

BACKGROUND OF THE INVENTION

Taurine can be referred to as 2-aminoethanesulfonic acid and is one of the amino sulfonic acids found in the tissues of many animals. Taurine is an extremely useful compound with beneficial pharmacological effects, such as detoxification, fatigue-relief, and nourishing and tonifying effects. As a result, taurine finds wide applications as an essential ingredient for human and animal nutrition.

Taurine is currently produced in an amount of over 50,000 tons per year from either ethylene oxide or monoethanolamine. At the present time, most taurine is produced from ethylene oxide, following a three-step process: (1) the addition reaction of ethylene oxide with sodium bisulfite to yield sodium isethionate; (2) the ammonolysis of sodium isethionate to yield sodium taurinate; (3) the neutralization with an acid, i.e., hydrochloric acid and, preferably, sulfuric acid, to generate taurine and inorganic salts.

Although the ethylene oxide process is well established and widely practiced in commercial production, the overall yield is not very high, less than 80%. Moreover, the process generates a large waste stream that is increasingly difficult to dispose of.

The first stage of the ethylene oxide process, the addition reaction of ethylene oxide with sodium bisulfite, is known to yield sodium isethionate in high yield, practically quantitative, as disclosed in U.S. Pat. No. 2,820,818 under described conditions.

Therefore, the problems encountered in the production of taurine from the ethylene oxide process arise from the ammonolysis of sodium isethionate and from the separation of taurine from sodium sulfate.

U.S. Pat. No. 1,932,907 discloses that sodium taurinate is obtained in a yield of 80%, when sodium isethionate undergoes ammonolysis reaction in a molar ratio of 1:6.8 for 2 hrs at 240 to 250° C. U.S. Pat. No. 1,999,614 describes the use of catalysts, i.e., sodium sulfate, sodium sulfite, and sodium carbonate, in the ammonolysis reaction. A mixture of sodium taurinate and sodium ditaurinate is obtained in a yield as high as 97%. However, the percentage for sodium taurinate and sodium ditaurinate in the mixture is not specified.

DD219023 describes detailed results on the product distribution of the ammonolysis reaction of sodium isethionate. When sodium isethionate undergoes the ammonolysis reaction with 25% aqueous ammonia in a molar ratio of 1:9 at about 280° C. for 45 minutes in the presence of sodium sulfate and sodium hydroxide as catalyst, the reaction products comprise 71% of sodium taurinate and 29% of sodium di- and tritaurinate.

WO01/77071 is directed to a process for the preparation of ditaurine by heating an aqueous solution of sodium taurinate at a temperature of 210° C. in the presence of a reaction medium. A mixture of sodium taurinate and sodium ditaurinate is obtained.

It is therefore concluded from the foregoing references that the ammonolysis of sodium isethionate invariably yields a mixture of sodium taurinate, sodium ditaurinate, and sodium tritaurinate. The percentage yield of sodium taurinate has not been more than 80%.

In order to obtain taurine from sodium taurinate, U.S. Pat. No. 2,693,488 discloses a method of using ion exchange resins involving a strongly acid ion exchange resin in hydrogen form, and then an anion exchange resin in basic form. This process is complicated and requires the use of a large quantity of acid and base to regenerate the ion exchange resins in each production cycle.

On the other hand, CN101508657, CN101508658, CN101508659, and CN101486669 describe a method of using sulfuric acid to neutralize sodium taurinate to obtain a solution of taurine and sodium sulfate. Crude taurine is easily obtained by filtration from a crystalline suspension of taurine after cooling. However, the waste mother liquor still contains taurine, sodium sulfate, and other unspecified organic impurities, which are identified as a mixture of sodium ditaurinate and sodium tritaurinate.

In the co-pending application Ser. No. 14/120,046, a novel process is disclosed for converting alkali ditaurinate or alkali tritaurinate, or their mixture, to alkali taurinate.

It is, therefore, an object of the present invention to disclose a process for the production of taurine from alkali isethionate in a high overall yield (i.e., greater than 90% to nearly quantitative). According to the process of the present invention, a solution of alkali ditaurinate or alkali tritaurinate, or their mixture, is mixed with alkali isethionate to increase the yield of the ammonolysis reaction by inhibiting the formation of alkali ditaurinate and tritaurinate byproducts and by converting the byproducts to alkali taurinate in the presence of one or more catalysts.

DESCRIPTION OF THE INVENTION

The present invention relates to a process for the production of taurine by the ammonolysis reaction of alkali isethionate in the presence of alkali ditaurinate or alkali tritaurinate, or their mixture, to inhibit the formation of byproducts, to increase the production yield, and to greatly reduce the waste discharge from the production process.

The process according to the present invention starts with mixing a solution of alkali ditaurinate or alkali tritaurinate, or their mixture, with alkali isethionate, followed by addition of an excess of ammonia. The ammonolysis is carried out at a temperature from 160° C. to 260° C. under the pressure from autogenous to 260 bars for 1 to 6 hours.

After the ammonolysis reaction, excess ammonia is dispelled from the reaction solution and reclaimed for reuse. A solution of alkali taurinate is obtained, along with alkali ditaurinate, alkali tritaurinate, and a trace amount of unreacted alkali isethionate.

The strongly basic solution is neutralized with an acid to pH 5-9 to yield a crystalline suspension of taurine in a solution of alkali salt, alkali ditaurinate, alkali tritaurinate, and a small amount of unreacted alkali isethionate. The initial suspension is optionally concentrated, then cooled to 28 to 35° C., to crystallize taurine. Taurine is obtained by means of solid-liquid separation.

The ratio of alkali ditaurinate, alkali tritaurinate, or their mixture, in relation to alkali isethionate can be varied from 0.01 to 10 by weight, preferably 0.1 to 1, more preferably 0.2-0.5, most preferably 0.3-0.4.

When the ratio is low, i.e., <0.1, a large amount of alkali isethionate is converted to alkali ditaurinate, instead of desired alkali taurinate, thus lowering the production yield and efficiency. When the ratio is too large, i.e., >1.0, the amount of the recycling byproducts becomes excessively large and the production capacity is lowered. Moreover, the cyclic process is not steady as the byproduct is indeed converted alkali taurinate.

Useful and effective catalysts are found among the alkali salts of hydroxide, carbonate, bicarbonate, hydrogen sulfate, sulfate, bisulfite, sulfite, nitrate, phosphate, chlorate, and perchlorate. Such salts are sodium hydroxide, lithium hydroxide, potassium hydroxide, lithium carbonate, lithium bicarbonate, sodium bicarbonate, sodium bicarbonate, potassium bicarbonate, lithium carbonate, sodium carbonate, potassium carbonate, lithium sulfate, sodium sulfate, potassium sulfate, lithium phosphate, sodium phosphate, potassium phosphate, lithium sulfite, sodium sulfite, and potassium sulfite.

The catalyst for the ammonolysis reaction of alkali isethionate can be one component or a combination of two or more components. Catalysts exogenous to the reaction system can be used, but catalysts inherently present in the production process are preferred. When sulfuric acid is used as a neutralizing acid, alkali salts of sulfate are preferred. Alkali salts of sulfite are preferred in the sulfur dioxide process.

Preferable catalysts are alkali hydroxide and the most preferable catalyst is sodium hydroxide.

The amount of the catalyst used is not limited, but is usually from 0.01 to 10 in molar ratio of the catalyst to alkali isethionate. The ratio is preferably in the range of 0.01 to 1, more preferably 0.1 to 0.5, most preferably 0.2 to 0.3. A suitable amount of catalyst can be selected by those skilled in the art for the ammonolysis reaction to complete in desired time.

The acid used in the neutralization process is selected from hydrochloric acid, hydrobromic acid, sulfuric acid, nitric acid, phosphoric acid, and organic carboxylic acids containing one to six carbons. Sulfuric acid is most preferably used.

Tables I to III demonstrate the effectiveness of the presence of alkali ditaurinate or alkali tritaurinate, or their mixture, on the ammonolysis of alkali isethionate to alkali taurinate, respectively. It becomes apparent that the conversion of alkali isethionate to alkali taurinate can reach nearly quantitative yield under disclosed conditions.

Table IV shows the effect of a different catalyst on the ammonolysis of alkali isethionate to alkali taurinate. When no catalyst is added to the ammonolysis reaction, low conversion of alkali isethionate is observed.

The process according to the present invention can be carried out discontinuously, semi-continuously, and continuously.

EXAMPLES

The following examples illustrate the practice of this invention but are not intended to limit its scope.

Example 1

This set of examples relates to the ammonolysis of sodium isethionate in the presence of sodium ditaurinate and in the presence of sodium hydroxide.

All examples are for 0.05 mole of sodium isethionate, dissolved in 35 mL of 20% aqueous ammonia solution in a molar ratio of 1:8 for sodium isethionate to ammonia. Calculated amount of sodium ditaurinate and sodium hydroxide is then added to the solution. The ammonolysis reaction is carried out in a 100 mL autoclave at 220° C. under autogenous pressure for two hours. The content of taurine, ditaurine, and tritaurine is assayed by HPLC analysis. The yields are calculated according to the following formula:

Taurinate Yield (%)=[Taurine]/[Sodium Isethionate]

Di+Tritaurinate Yield (%)=[Di+Tritaurine−Added Ditaurine]/[Sodium Isethionate]

TABLE I

Ammonolysis of Sodium Isethionate in the Presence of Sodium Ditaurinate

| Ex | Ditaurinate/ Isethionate (ratio by weight) | NaOH/ Isethionate (ratio by weight) | Taurinate (molar yield %) | Di + Tritaurinate (molar yield %) |
|---|---|---|---|---|
| 1 | 0 | 0.01 | 75 | 24 |
| 2 | 0.1 | 0.01 | 84 | 15 |
| 3 | 0.2 | 0.01 | 86 | 14 |
| 4 | 0.3 | 0.01 | 87 | 13 |
| 5 | 0.3 | 0.02 | 91 | 9 |
| 6 | 0.3 | 0.03 | 93 | 7 |
| 7 | 0.3 | 0.04 | 95 | 5 |
| 8 | 0.3 | 0.05 | 98 | 2 |
| 9 | 0.5 | 0.15 | 112 | −12 |
| 10 | 1.0 | 0.20 | 145 | −45 |

Example 2

This set of examples relates to the ammonolysis of sodium isethionate in the presence of sodium tritaurinate and in the presence of sodium hydroxide.

All examples are for 0.05 mole of sodium isethionate, dissolved in 35 mL of 20% aqueous ammonia solution in a molar ratio of 1:8 for sodium isethionate to ammonia. Calculated amount of sodium tritaurinate and sodium hydroxide is then added to the solution. The ammonolysis reaction is carried out in a 100 mL autoclave at 220° C. under autogenous pressure for two hours. The content of taurine, ditaurine, and tritaurine is assayed by HPLC analysis. The yields are calculated according to the following formula:

Taurinate Yield (%)=[Taurine]/[Sodium Isethionate]

Di+Tritaurinate Yield (%)=[Di+Tritaurine−Added Tritaurine]/[Sodium Isethionate]

TABLE II

Ammonolysis of Sodium Isethionate in the Presence of Sodium Tritaurinate

| Ex | Tritaurinate/ Isethionate (ratio by weight) | NaOH/ Isethionate (ratio by weight) | Taurinate (molar yield%) | Di + Tritaurinate (molar yield %) |
|---|---|---|---|---|
| 11 | 0 | 0.01 | 76 | 24 |
| 12 | 0.1 | 0.01 | 83 | 16 |
| 13 | 0.2 | 0.01 | 86 | 14 |
| 14 | 0.3 | 0.01 | 87 | 13 |
| 15 | 0.3 | 0.02 | 88 | 11 |
| 16 | 0.3 | 0.03 | 94 | 6 |
| 17 | 0.3 | 0.04 | 94 | 5 |
| 18 | 0.3 | 0.05 | 98 | 2 |
| 19 | 0.5 | 0.15 | 121 | −20 |
| 20 | 1.0 | 0.20 | 151 | −49 |

Example 3

This set of examples relates to the ammonolysis of sodium isethionate in the presence of a mixture of sodium ditaurinate and sodium tritaurinate obtained from the mother liquor of taurine crystallization and in the presence of sodium hydroxide and sodium sulfate.

All examples are for 0.05 mole of sodium isethionate, dissolved in 35 mL of 20% aqueous ammonia solution in a molar ratio of 1:8 for sodium isethionate to ammonia. Calculated amount sodium hydroxide is then added to the solution. A mixture of sodium ditaurinate and sodium tritaurinate, obtained from the crystallization mother liquor described as in application Ser. No. 14/120,046 is used. The ammonolysis reaction is carried out in a 100 mL autoclave at 220° C. under autogenous pressure for two hours. The content of taurine, ditaurine, and tritaurine is assayed by HPLC analysis. The yields are calculated according to the following formula:

Taurinate Yield (%)=[Taurine]/[Sodium Isethionate]

Di+Tritaurinate Yield (%)=[Di+Tritaurine−(Added Di+Tritaurine)]/[Sodium Isethionate]

TABLE III

Ammonolysis of Sodium Isethionate in the Presence of a Mixture of Sodium Ditaurinate and Sodium Tritaurinate

| Ex | (Di + Tritaurinate)/ Isethionate (ratio by weight) | NaOH/ Isethionate (ratio by weight) | Taurinate (molar yield%) | Di + Tritaurinate (molar yield %) |
|---|---|---|---|---|
| 21 | 0 | 0.01 | 81 | 19 |
| 22 | 0.1 | 0.01 | 84 | 16 |
| 23 | 0.2 | 0.01 | 87 | 12 |
| 24 | 0.3 | 0.01 | 87 | 13 |
| 25 | 0.3 | 0.02 | 88 | 11 |
| 26 | 0.3 | 0.03 | 95 | 4 |
| 27 | 0.3 | 0.04 | 96 | 4 |
| 28 | 0.3 | 0.05 | 98 | 2 |
| 29 | 0.5 | 0.15 | 126 | −26 |
| 30 | 1.0 | 0.20 | 154 | −53 |

Example 4

This set of examples shows the effect of a different catalyst on the ammonolysis of sodium isethionate in the presence of a mixture of sodium ditaurinate and sodium tritaurinate obtained from the mother liquor of taurine crystallization.

All examples are for 0.05 mole of sodium isethionate, dissolved in 35 mL of 20% aqueous ammonia solution in a molar ratio of 1:8 for sodium isethionate to ammonia. Calculated amount catalyst and a mixture of sodium ditaurinate and sodium tritaurinate, obtained from the crystallization mother liquor described as in application Ser. No. 14/120,046, are added to the solution. The ratio of (di+tritaurinate)/isethionate by weight are fixed at 0.3. The ammonolysis reaction is carried out in a 100 mL autoclave at 220° C. under autogenous pressure for two hours. The content of taurine, ditaurine, and tritaurine is assayed by HPLC analysis. The yields are calculated according to the following formula:

Taurinate Yield (%)=[Taurine]/[Sodium Isethionate]

Di+Tritaurinate Yield (%)=[Di+Tritaurine−(Added Di+Tritaurine)]/[Sodium Isethionate]

TABLE IV

Effect of Catalyst on Ammonolysis of Sodium Isethionate in the Presence of a Mixture of Sodium Ditaurinate and Sodium Tritaurinate

| Ex | Catalyst | Catalyst/ Isethionate (ratio by weight) | Taurinate (molar yield%) | Di + Tritaurinate (molar yield %) |
|---|---|---|---|---|
| 31 | None | 0 | 55 | 12 |
| 32 | Sodium carbonate | 0.15 | 96 | 4 |
| 33 | Sodium sulfite | 0.15 | 95 | 4 |
| 34 | Potassium hydroxide | 0.10 | 97 | 3 |
| 35 | Potassium carbonate | 0.15 | 94 | 6 |
| 36 | Potassium sulfite | 0.10 | 94 | 6 |
| 37 | Lithium hydroxide | 0.03 | 95 | 4 |
| 38 | Lithium carbonate | 0.10 | 93 | 7 |
| 39 | Sodium phosphate | 0.15 | 97 | 3 |
| 40 | Potassium phosphate | 0.15 | 96 | 4 |
| 41 | Potassium acetate | 0.20 | 96 | 4 |
| 42 | Sodium acetate | 0.20 | 96 | 4 |

It will be understood that the foregoing examples and explanation are for illustrative purposes only and that various modifications of the present invention will be self-evident to those skilled in the art. Such modifications are to be included within the spirit and purview of this application and the scope of the appended claims.

What is claimed is:

1. A process for producing alkali taurinate from alkali isethionate in molar yield of at least 80% on the basis of alkali isethionate, comprising:
    (a) mixing a solution comprised of alkali ditaurinate or alkali tritaurinate or their mixture with alkali isethionate in the presence of a catalyst, wherein the ratio of alkali ditaurinate or alkali tritaurinate or their mixture is from 0.1 to 1.0 by weight on the basis of alkali isethionate, and wherein the catalyst is an alkali hydroxide and the amount of the alkali hydroxide is from 0.1 to 1.0 in molar ratio on the basis of alkali isethionate;
    (b) adding excess ammonia to the solution of step (a);
    (c) subjecting the solution of step (b) to an ammonolysis; and
    (d) removing excess ammonia from the solution of step (c) to obtain a solution comprising alkali taurinate.

2. The process of claim 1, wherein a process for producing taurine further comprises the steps of:
    (e) neutralizing the solution comprised of alkali taurinate with an acid to form a solution containing a crystalline suspension of taurine, wherein the solution has a pH of 5-9; and (f) separating the taurine from the solution to yield a mother liquor.

3. The process of claim 2, wherein the mother liquor obtained from step (f) is mixed with alkali isethionate to form a solution comprised of alkali isethionate, alkali ditaurinate, and alkali tritaurinate that is then recycled into the process, which comprises:
 (a) adding an alkali hydroxide to an aqueous solution comprising alkali isethionate, alkali ditaurinate, and alkali tritaurinate, wherein the molar amount of alkali hydroxide in the solution is at least equal to the molar amount of total taurinates comprising alkali ditaurinate and alkali tritaurinate;
 (b) adding excess ammonia to the aqueous solution comprised of alkali isethionate, dialkali ditaurinate, and trialkali tritaurinate;
 (c) subjecting the solution comprised of alkali isethionate, dialkali ditaurinate, and trialkali tritaurinate to an ammonolysis reaction; and
 (d) removing excess ammonia from the solution to obtain a solution comprising alkali taurinate.

4. The process of claim 1, wherein the weight ratio of the alkali ditaurinate and the alkali tritaurinate to the alkali isethionate is between 0.2 and 1.0.

5. The process of claim 2, wherein the acid is selected from the group consisting of hydrobromic, hydrochloric, sulfuric acid, nitric acid, or phosphoric acid, and mixtures thereof.

6. The process of claim 2, wherein the acid is sulfuric acid.

7. The process of claim 1, wherein the alkali is lithium, sodium, potassium, or a mixture thereof.

8. The process of claim 1, wherein the aqueous solution comprised of alkali isethionate, alkali ditaurinate, and alkali tritaurinate is the mother liquor after taurine separation.

9. The process of claim 1, wherein the alkali is sodium.

\* \* \* \* \*